US00PP21437P2

(12) United States Plant Patent

Laviana

(10) Patent No.: US PP21,437 P2

(45) Date of Patent: Nov. 2, 2010

(54) *KNAUTIA* PLANT NAMED 'THUNDER AND LIGHTNING'

(50) Latin Name: *Knautia macedonica*
Varietal Denomination: Thunder and Lightning

(75) Inventor: Marc R. Laviana, Kensington, CT (US)

(73) Assignee: Sunny Border Nurseries CT (US)

( * ) Notice: Subject to any disclaimer, the term of this patent is extended or adjusted under 35 U.S.C. 154(b) by 0 days.

(21) Appl. No.: 12/584,874

(22) Filed: Sep. 14, 2009

(51) Int. Cl.
*A01H 5/00* (2006.01)

(52) U.S. Cl. ..... Plt./263.1

(58) Field of Classification Search ..... Plt./478, Plt./263.1

See application file for complete search history.

*Primary Examiner*—Susan B McCormick Ewoldt
(74) *Attorney, Agent, or Firm*—Penny J. Aguirre

(57) ABSTRACT

A new cultivar of *Knautia* 'Thunder and Lightning' characterized by variegated foliage with green centers and white margins, its short stature, its long blooming period and its bright red-purple inflorescences that are subtended by variegated involucral bracts.

1 Drawing Sheet

Botanical classification: *Knautia macedonica.*

Variety denomination: 'Thunder and Lightning'

BACKGROUND OF THE INVENTION

The present invention relates to a new and distinct cultivar of *Knautia macedonica* named 'Thunder and Lightning' and will be referred to hereinafter by its cultivar name, 'Thunder and Lightning'.

The inventor discovered the new cultivar, 'Thunder and Lightning' in October of 2007 in a container in his nursery in Kensington, Conn. 'Thunder and Lightning' arose as a naturally occurring chimeral mutation of an unnamed plant of *Knautia macedonica.*

Asexual reproduction of the new cultivar was first accomplished by culm cutting in Kensington, Conn. in 2007 by the Inventor. The characteristics of this cultivar have been determined to be stable and are reproduced true to type in successive generations.

SUMMARY OF THE INVENTION

The following traits have been repeatedly observed and are determined to be the characteristics of 'Thunder and Lightning'. These characteristics in combination distinguish 'Thunder and Lightning' as a new and distinct cultivar of *Knautia.*

1. 'Thunder and Lightning' exhibits variegated foliage with green centers and white margins.
2. 'Thunder and Lightning' exhibits a plant height that is shorter than the species.
3. 'Thunder and Lightning' exhibits bright red-purple inflorescences that are subtended by variegated involucral bracts.
4. 'Thunder and Lightning' blooms from early summer until frost.

'Thunder and Lightning' can be compared to its parent species, *Knautia macedonica*, which has foliage that is non-variegated. There are no other cultivars of *Knautia macedonica* that exhibit variegated foliage known to the Inventor.

BRIEF DESCRIPTION OF THE DRAWING

The accompanying colored photograph illustrates the overall appearance and distinct characteristics of one-year old plant of the new *Knautia* as grown in a one-gallon container in Kensington, Conn.

The photograph in FIG. 1 illustrates the variegated foliage, inflorescences, and short stature.

Figure 1:
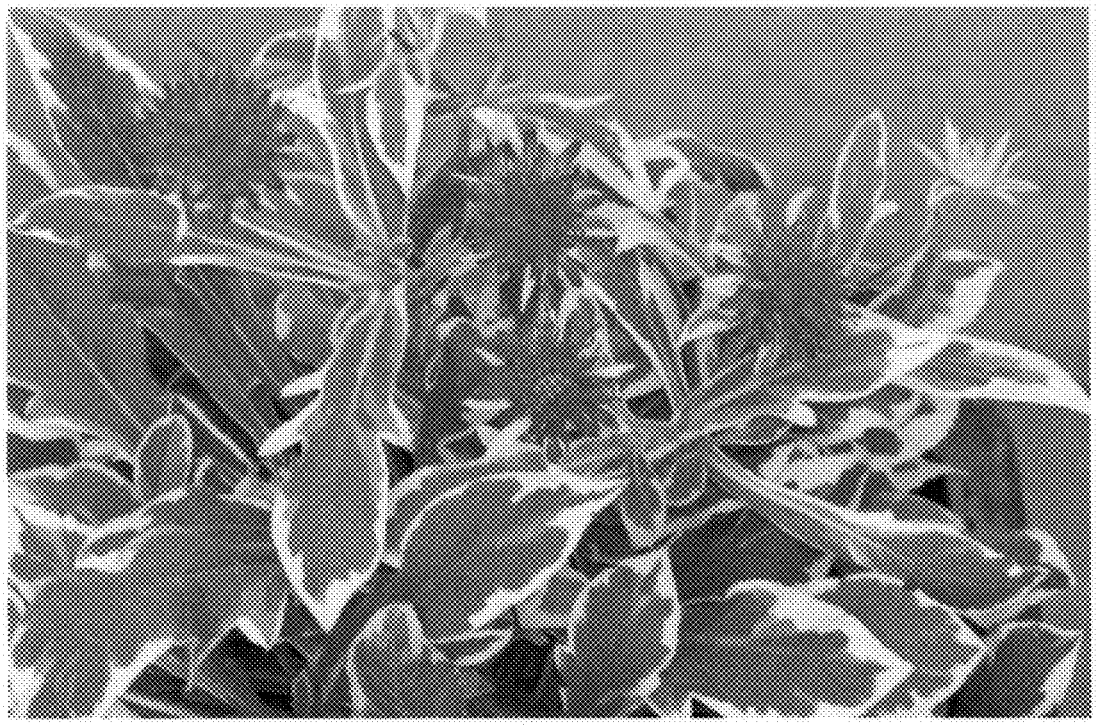

The colors in the photograph may differ slightly from the color values cited in the detailed botanical description, which accurately describe the colors of the new *Knautia.*

DETAILED BOTANICAL DESCRIPTION

The following is a detailed description of one year-old plant of the new cultivar as grown in Kensington, Conn. The color determination is in accordance with The 2007 R.H.S. Colour Chart of The Royal Horticultural Society, London, England, except where general color terms of ordinary dictionary significance are used.

General description:

*Blooming period.*—May through September in Connecticut.

*Plant habit.*—Herbaceous perennial herb, upright with extended flowering stems.

*Height and spread.*—Reaches about 30 cm in height and 26 cm in width.

*Hardiness.*—Cold hardy at least to U.S.D.A Zones 5 to 9.

*Disease and pest resistance.*—No susceptibility or resistance to diseases or pests has been observed.

*Root description.*—Fibrous.

Growth and propagation:

*Propagation.*—Crown cuttings.

*Growth rate.*—Moderate.

Stem description:

*Stem shape.*—Oval.

*Stem color.*—137D.

*Stem size.*—An average of 25 cm in length (including peduncle) on solitary stems, 30 cm in length on center stem of cymes with side branches an average of 14 cm in length, an average of 3 mm in length.

*Stem surface.*—Scabrous.
*Stem strength.*—Strong, held upright.
*Branching habit.*—Branched near base into a center stem and two side cymes.

Foliage description:
*Leaf division.*—Simple.
*Leaf shape.*—Oblanceolate.
*Leaf base.*—Attenuate.
*Leaf apex.*—Acute.
*Leaf margin.*—Entire to pinnatifid (average of 2 lobes per side).
*Leaf venation.*—Pinnate, mid rib on upper surface 146D and 138B on lower surface, other veins match leaf color.
*Leaf attachment.*—Sessile and clasping to stem.
*Leaf arrangement.*—Opposite.
*Leaf surface.*—Pubescent, upper and lower surfaces.
*Leaf color.*—Variegated, young and mature upper surface; centers 138A and margins 4D, young and mature lower surface; centers 138B and margins 4D.
*Leaf size.*—Basal and lower stem leaves average 7 cm in length and 2 cm in width, stem leaves average 8 cm in length and 2.5 cm in width.
*Leaf number.*—Average of 14 per main branched stem.
*Leaf fragrance.*—None.
*Petiole.*—None.

Flower description:
*Inflorescence type.*—Flat topped heads subtended by leafy, involucral bracts, solitary or in cyme.
*Lastingness of inflorescence.*—Average of 10 days.
*Inflorescence size.*—An average of 1.7 cm in height and 3 cm in diameter.
*Inflorescence fragrance.*—None.
*Flower number.*—Average of 85 per flowering stem.
*Flower form.*—Tubular with basal one third fused.
*Flower aspect.*—Upright.
*Flower buds.*—Average of 2.5 mm in length, average of 1.5 mm in diameter, 138C in color, obovate in shape.
*Flower size.*—Average of 7 mm in length and 3 mm in diameter.
*Petals.*—4, lanceolate in shape, N79C in color on inner and outer surface and drying to N92A on both surfaces after maturation, surface is dull with fine white hairs about 1 mm in length on outer surface, margins entire, apex acute, base fused, an average of 2 mm in length and 0.8 mm in width.
*Calyx.*—Campanulate, an average of 2 mm in length and 1.5 mm in diameter, comprised of upright sepals that are un-fused and overlapping at base.
*Sepals.*—8, linear to lanceolate, an average of 2 mm length, 0.3 mm in width, entire and pubescent margin, scabrous surface, attenuate apex, truncate base, 145D in color and translucent towards apex.
*Peduncles.*—An average of 20 cm in length and 2 mm in diameter on terminal flowering stems and 6 cm in length and 2 mm in diameter on lateral flowering stems, pubescent surface, 138A to 147A in color and striped with N186C, pubescent surface.
*Pedicels.*—None.
*Involucral bracts.*—An average of 13, lanceolate in shape, about 1.8 cm in depth and 4 mm in width, color; variegated with centers 138B and wide margins 4D, surface moderately covered with fine hairs about 2 mm in length, apex acute, margins entire, held nearly horizontally.
*Receptical.*—5 mm in diameter and 3 mm in height, 151D in color.

Reproductive organs:
*Gynoecium.*—1 pistil, about 7 mm in length, stigma is club-shaped and N79A in color, style is about 6 mm in length, N81C in color, ovary is 143B in color.
*Androcoecium.*—2 stamens, elliptic in shape, about 0.7 mm in length and N99C in color, filament is about 2 mm in length and 91D in color, no pollen was observed.
*Fruit/seeds.*—No fruit set (or seeds) have been observed to date.

It is claimed:

1. A new and distinct cultivar of *Knautia* plant named 'Thunder and Lightning' as herein illustrated and described.

* * * * *